US008956420B2

(12) United States Patent
Varley

(10) Patent No.: US 8,956,420 B2
(45) Date of Patent: Feb. 17, 2015

(54) MYOELECTRIC ELECTRODE ASSEMBLY

(71) Applicant: Edward William Varley, Huddersfield (GB)

(72) Inventor: Edward William Varley, Huddersfield (GB)

(73) Assignee: Hugh Steeper Limited, Leeds (GB)

( * ) Notice: Subject to any disclaimer, the term of this patent is extended or adjusted under 35 U.S.C. 154(b) by 60 days.

(21) Appl. No.: 13/747,713

(22) Filed: Jan. 23, 2013

(65) Prior Publication Data

US 2013/0197669 A1    Aug. 1, 2013

(30) Foreign Application Priority Data

Jan. 27, 2012    (GB) .................................... 1201441.1

(51) Int. Cl.
| A61F 2/72 | (2006.01) |
| A61B 5/0492 | (2006.01) |
| A61F 2/80 | (2006.01) |
| A61B 5/0488 | (2006.01) |
| A61F 2/76 | (2006.01) |
| A61F 2/50 | (2006.01) |

(52) U.S. Cl.
CPC ................. *A61F 2/72* (2013.01); *A61B 5/0492* (2013.01); *A61F 2/80* (2013.01); *A61B 5/04888* (2013.01); *A61F 2/76* (2013.01); *A61F 2002/5083* (2013.01); *A61F 2002/802* (2013.01)

USPC ............................................................ 623/25

(58) Field of Classification Search
CPC ............................. A61F 2/72; A61B 5/04888
USPC ......................... 277/919; 174/17 CT; 623/25
See application file for complete search history.

(56) References Cited

U.S. PATENT DOCUMENTS

| 4,829,364 A | * | 5/1989 | Ohdate ........................ 257/689 |
| 5,817,030 A | | 10/1998 | Tarjan et al. |
| 2009/0216339 A1 | | 8/2009 | Hanson et al. |

FOREIGN PATENT DOCUMENTS

| CA | 2 786 932 A1 | * | 7/2011 | ................ A61F 2/72 |
| DE | 10 2010 005462 | | 7/2011 | |
| EP | 1 857 081 | | 11/2007 | |
| GB | 1 191 301 | | 5/1970 | |

* cited by examiner

*Primary Examiner* — David H Willse
(74) *Attorney, Agent, or Firm* — Clark & Brody

(57) ABSTRACT

A myoelectric electrode assembly for a prosthesis comprising a retention ring adapted to be inserted into a correspondingly shaped aperture in the wall of the prosthesis. The assembly also has a myoelectric electrode unit held within the retention ring by a gasket which surrounds the electrode unit and is in sealing engagement therewith. A portion of the gasket is received in and sealingly engages with an annular recess around the inside of the retention ring.

7 Claims, 6 Drawing Sheets

MYOELECTRIC ELECTRODE ASSEMBLY

The present invention relates to a myoelectric electrode assembly for a prosthesis.

Such an assembly has been constructed hitherto to enable an electric signal to be transferred from the stump of an amputee to control apparatus of the prosthesis.

Since the prosthesis is attached to such a stump in a satisfactorily firm fashion by creating a vacuum between a part of the prosthesis and the stump, there needs to be a sufficient seal between the myoelectric electrode assembly and surrounding portions of the prosthesis to enable such a vacuum to be created.

One such construction of a myoelectric electrode assembly is described in EP-A-1857081. This describes a myoelectric electrode unit received within a resilient fitting having flange portions which extend on opposite sides of the wall of a prosthesis to effect a seal. This requires a relatively high degree of precision in the size of the aperture in the wall of the prosthesis.

The present invention seeks to provide a remedy.

Accordingly, the present invention is directed to a myoelectric electrode assembly for a prosthesis comprising a retention ring adapted to be inserted into a correspondingly shaped aperture in the wall of the prosthesis, and a myoelectric electrode unit held within the retention ring by means of a gasket which surrounds the electrode unit and is in sealing engagement therewith and a portion of which is received in and sealingly engages with an annular recess around the inside of the retention ring.

As a result, the precision for the sealing engagements is provided in the assembly itself, and provided the shape of an aperture into which the assembly is inserted is not too much larger than the assembly itself, the retention ring can be permanently fixed to the wall of the prosthesis by lamination or adhesive or other material built up between the wall of the prosthesis and the retention ring.

The said portion may comprise an annular flange which projects outwardly from a periphery of the gasket.

The gasket is preferably made of a resilient material, preferably a natural or synthetic rubber material, to facilitate removal and replacement of the myoelectric electrode unit.

The myoelectric unit may be generally rectangular as viewed from above, so that the gasket and the retention ring may be correspondingly rectangular to provide generally rectangular apertures.

The flange may be generally T-shaped in section with a first portion extending away from the myoelectric electrode unit, and a second portion at the distal end of the first portion extending transversely thereof, with the second portion being received in the said annular recess.

Formations may be provided on the myoelectric electrode unit and the gasket so that those of the former interlock with those of the latter to secure the myoelectric electrode unit in position within the gasket.

The present invention extends to a prosthesis having a myoelectric electrode assembly in accordance with the present invention.

An example of a myoelectric electrode assembly will now be described in greater detail with reference to the accompanying drawings, in which.

Figure 1:
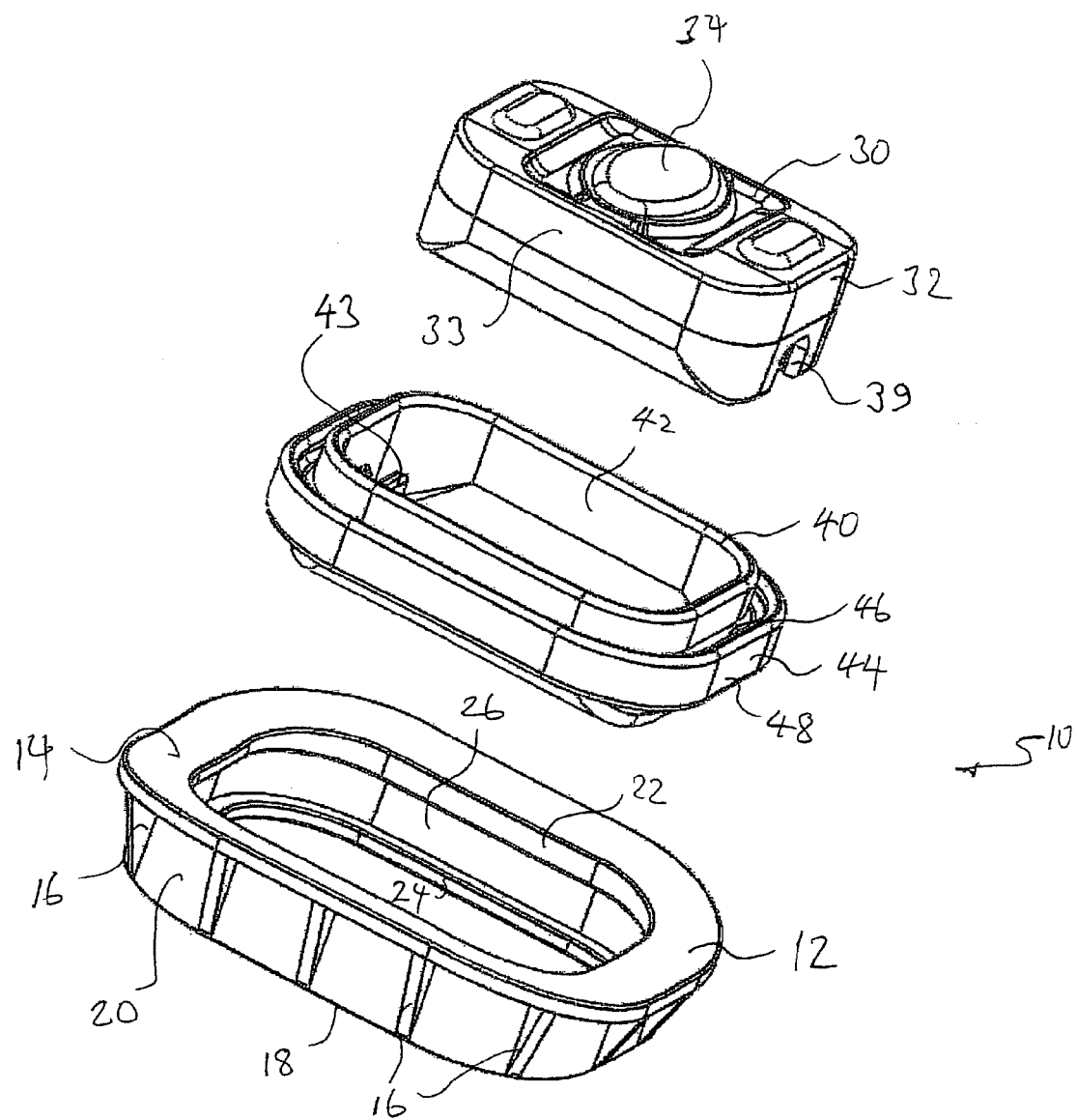
FIG. 1 shows a perspective exploded view of an assembly embodying the present invention.
Figure 2:
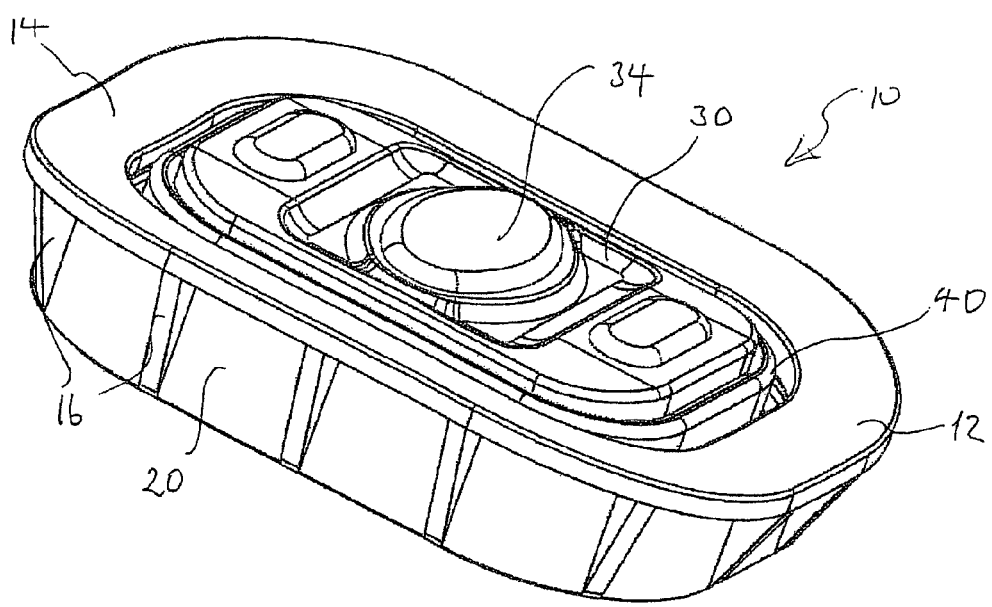
FIG. 2 shows a perspective view from one side of the assembly in an assembled condition.
Figure 3:
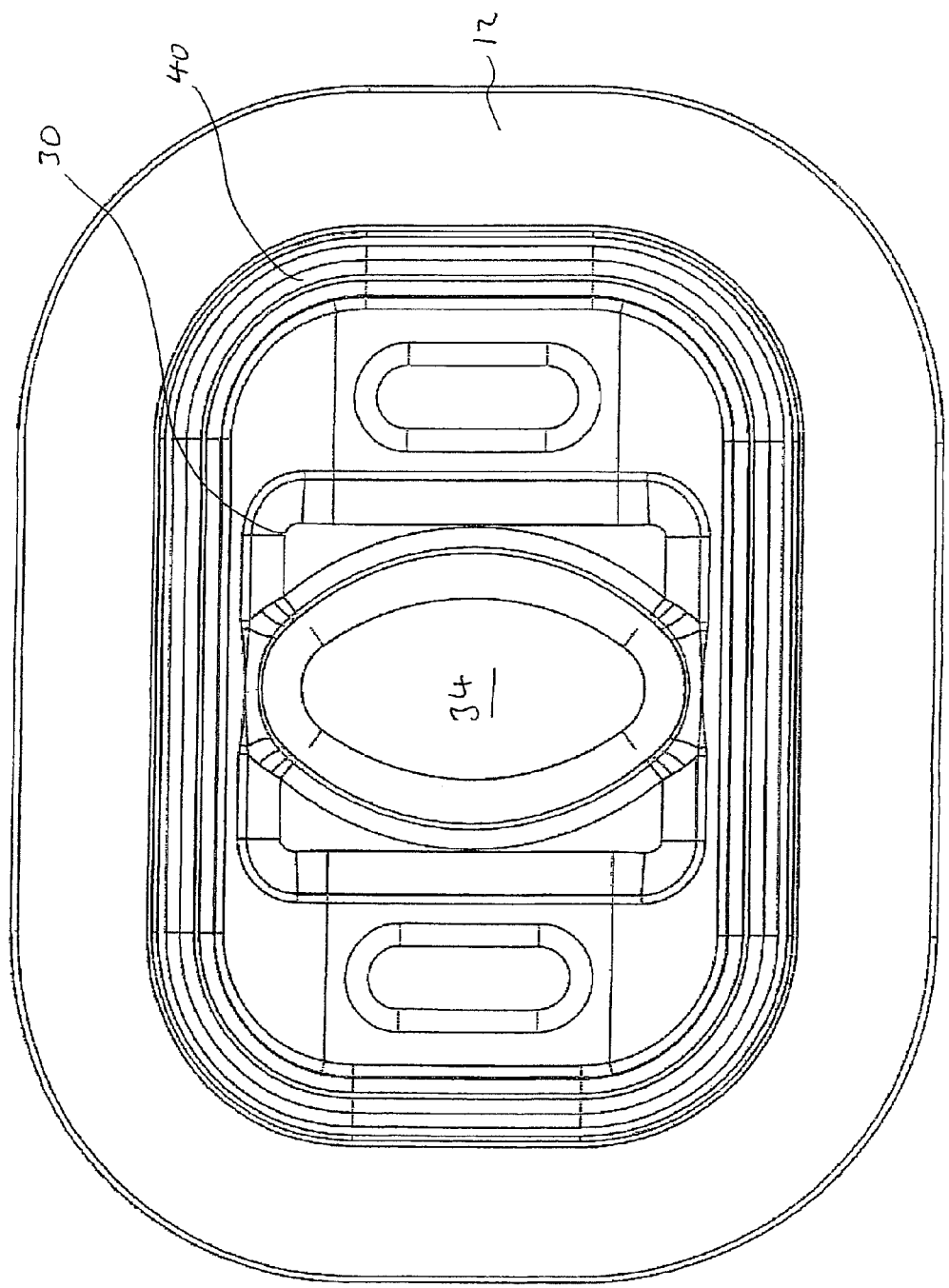
FIG. 3 shows on a different scale a view of the assembly shown in FIG. 2 from an intended inner position.
Figure 4:
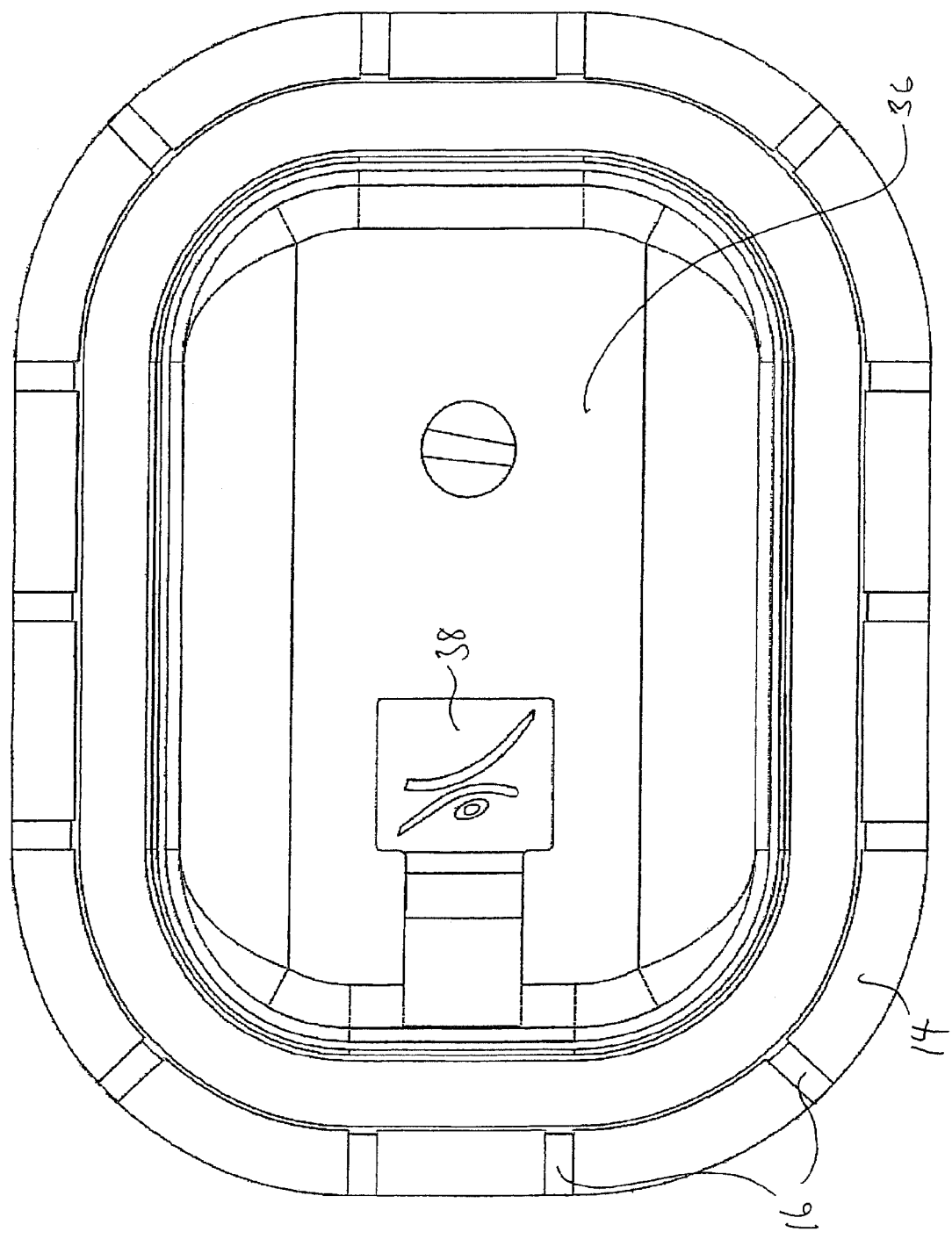
FIG. 4 shows a view of the assembly shown in FIG. 2 from an intended outer position.
Figure 5:
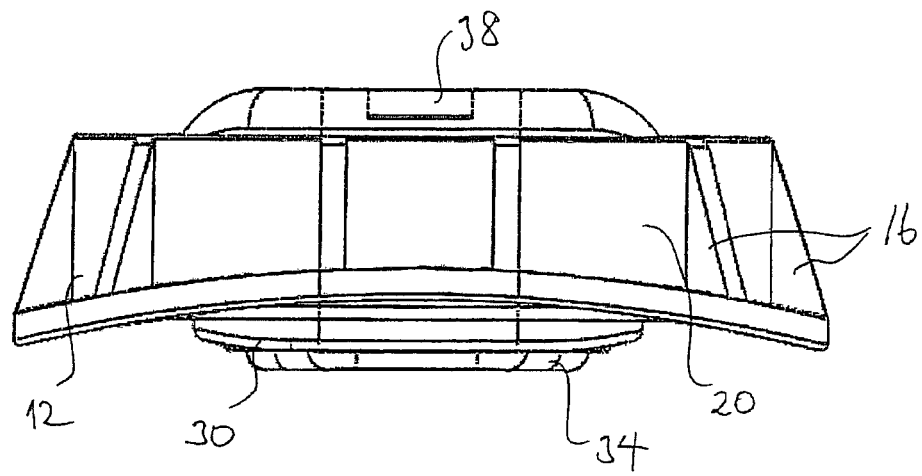
FIG. 5 shows an end view of the assembly shown in FIG. 2.
Figure 6:
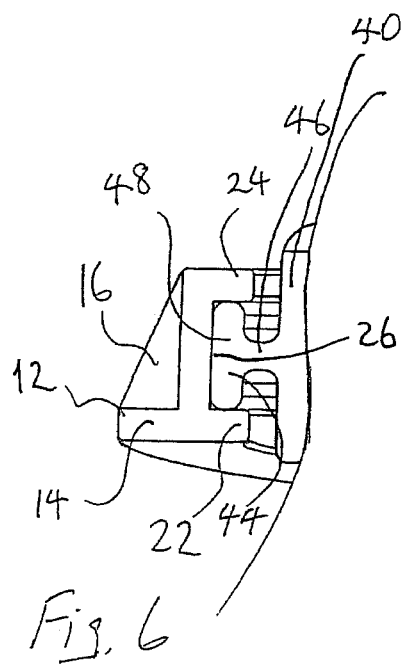
FIG. 6 shows a cross-sectional view of part of the assembly shown in FIG. 2.
Figure 7:
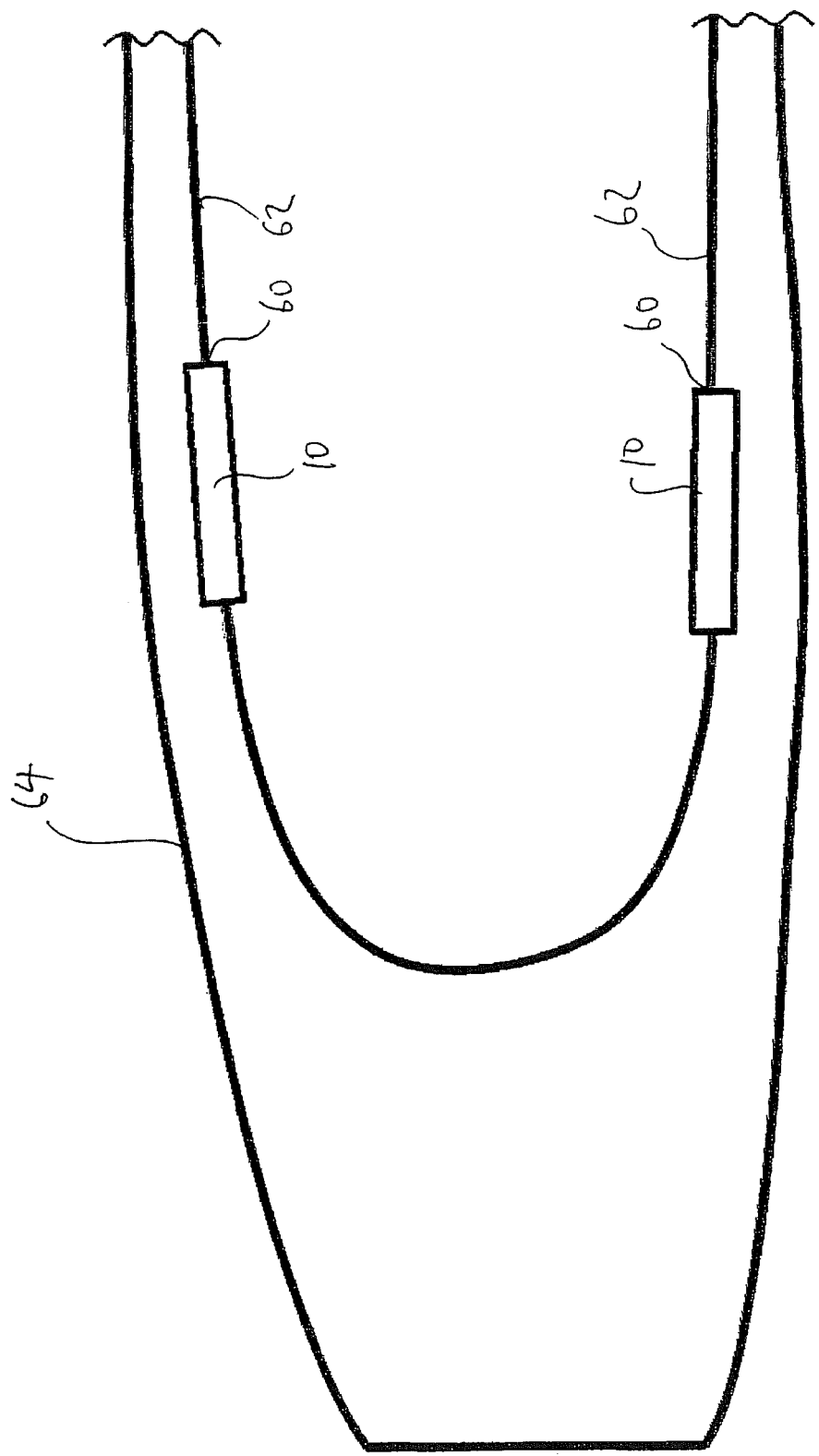
FIG. 7 shows a diagrammatic axial sectional view of a prosthesis provided with an assembly as shown in FIGS. 1 to 6.

A myoelectric electrode assembly 10 shown in FIGS. 1 to 6 comprises a generally rectangular plastics retention ring 12 (with rounded corners) having a flange 14 on an intended inward side thereof and tapering ribs 16 which taper in a direction away from the flange 14 and which extend from that flange to an intended outward side 18 of the retention ring 12 on a side wall 20 thereof. Inner and outer lips 22 and 24 define an annular recess which is rectangular in section and which extends around the inside of the retention ring 12.

A myoelectric electrode unit 30 of the assembly, which unit has a generally rectangular periphery 33 (with rounded corners), comprises a synthetic plastics housing 32 outwardly from which protrudes a myoelectric electrode 34 in an intended inward direction when the assembly is inserted in the wall of a prosthesis. An intended outward side 36 of the myoelectric electrode unit 30 is provided with connecting means 38 by which an electrical connection can be made to the myoelectric electrode 34 from the outward side of the prosthesis wall when the assembly is fitted for use.

The unit 30 is provided with engagement formations 39.

The myoelectric electrode unit 30 is held within the retention ring 12 by means of a rubber gasket 40. This forms a tight sealing fit around its inside surfaces 42 around the periphery 33 of the housing 32 such as to form a sealing engagement therewith. Inwardly extending engagement formations 43 (only one of which is visible in FIG. 1) on the inside of the gasket 40 engage the formations 39 to interlock therewith and secure the myoelectric electrode unit 30 in position within the gasket 40. The gasket 40 is also formed with an outwardly projecting flange 44 which is generally T-shaped in section having a first portion 46 which extends outwardly in a direction away from the unit 30, and a second portion 48 which is elongate in cross-section and which extends transversely of the portion 46 and is integral with an outer end of the portion 46 considering it in section, or an outer edge of the portion 46 considering it as a whole.

The portion 48 of the flange 44 is received in the groove 26 and is in sealing engagement therewith, so that the outer face of the portion 48 of the flange 44 is in contact with the innermost face of the recess 26, and the edges of the portion 48 abut the lips 22 and 24 on the sides thereof that define the sides of the recess 26.

When the assembly 10 shown in FIGS. 1 to 6 is in use, the retention ring 12 is inserted in a correspondingly shaped aperture 60 in a wall 62 of a prosthesis 64. It will be appreciated that the wall 62 is an inner wall of the prosthesis 64 that receives a stump of the amputee. The wall is built up around the aperture 60 by lamination and/or adhesive to form a rigid and secure attachment of the retention ring 12 within the wall 62. The lamination and/or adhesive forms a seal between the wall 60 and the retention ring 12. The adherence of the retention ring 12 to the lamination and/or adhesive is facilitated by a keying provided by the ribs 16 of the retention ring 12.

Numerous variations and modifications to the illustrated assembly will occur to the reader without taking the resulting construction outside the scope of the present invention. To provide one example only, the portion 48 may be circular in section to provide an O-ring around the rest of the gasket 40, and this may be received in a recess 26 having a part circular cross-section to receive such an O-ring in sealing engagement. Alternatively, the unit 30 may be provided with a recess around its periphery, and the recess 26 may be correspondingly shaped so that the gasket 40 may instead be a simple O-ring.

The invention claimed is:

1. A prosthesis having a wall and a myoelectric electrode assembly comprising a retention ring in which the wall of the prosthesis has an aperture of corresponding shape to the retention ring, and in which the retention ring is inserted in the said aperture, the myoelectric electrode assembly further comprising a myoelectric electrode unit held within the retention ring by means of a gasket which surrounds the myoelectric electrode unit and is in sealing engagement therewith and a portion of which is received in and sealingly engages with an annular recess around the inside of the retention ring.

2. A prosthesis according to claim 1, wherein the said portion comprises an annular flange which projects outwardly from a periphery of the gasket.

3. A prosthesis according to claim 1, wherein the gasket is made of a resilient material to facilitate removal and replacement of the myoelectric electrode unit.

4. A prosthesis according to claim 1, wherein the gasket is made of a natural or synthetic rubber material.

5. A prosthesis according to claim 1, wherein the myoelectric unit is generally rectangular as viewed from above, so that the gasket and the retention ring are correspondingly rectangular to provide generally rectangular apertures.

6. A prosthesis according to claim 2, wherein the flange is generally T-shaped in section with a first portion extending away from the myoelectric electrode unit, and a second portion at the distal end of the first portion extending transversely thereof, with the second portion being received in the said annular recess.

7. A prosthesis according to claim 1, wherein formations are provided on the myoelectric electrode unit and the gasket so that those of the former interlock with those of the latter to secure the myoelectric electrode unit in position within the gasket.

* * * * *